(12) United States Patent
Hack et al.

(10) Patent No.: US 7,740,477 B2
(45) Date of Patent: Jun. 22, 2010

(54) DENTAL DEVICE FOR THE INVESTIGATION OF THE OPTICAL PROPERTIES OF TOOTH TISSUE

(75) Inventors: Alexander Hack, Biberach (DE); Sven Erdmann, Ulm (DE); Hans Heckenberger, Assmannshardt (DE)

(73) Assignee: Kaltenbach & Voigt GmbH, Biberach (DE)

( * ) Notice: Subject to any disclaimer, the term of this patent is extended or adjusted under 35 U.S.C. 154(b) by 840 days.

(21) Appl. No.: 11/126,768

(22) Filed: May 11, 2005

(65) Prior Publication Data
US 2005/0255424 A1    Nov. 17, 2005

(30) Foreign Application Priority Data
May 14, 2004   (DE)   ........................ 10 2004 024 165

(51) Int. Cl.
*A61C 19/10*   (2006.01)
(52) U.S. Cl. .......................................... 433/26; 356/402
(58) Field of Classification Search ................... 433/29, 433/114, 26; 356/402, 406, 407
See application file for complete search history.

(56) References Cited

U.S. PATENT DOCUMENTS

| 5,035,508 | A | * | 7/1991 | Carter et al. ................. 356/416 |
| 5,921,776 | A | * | 7/1999 | Heilbrunn .................... 433/116 |
| 5,961,327 | A | * | 10/1999 | Lohn .......................... 433/80 |
| 6,053,731 | A | | 4/2000 | Heckenberger ............... 433/29 |
| 6,094,272 | A | * | 7/2000 | Okamoto ..................... 356/402 |
| 6,102,704 | A | | 8/2000 | Eibofner et al. ............. 433/215 |
| 6,157,454 | A | | 12/2000 | Wagner et al. ............... 356/407 |
| 6,201,880 | B1 | * | 3/2001 | Elbaum et al. ............... 382/100 |
| 6,276,933 | B1 | * | 8/2001 | Melnyk et al. ................ 433/26 |
| 6,398,424 | B1 | * | 6/2002 | Jin et al. ........................ 385/83 |
| 6,485,300 | B1 | * | 11/2002 | Muller et al. .................. 433/29 |
| 6,561,802 | B2 | | 5/2003 | Alexander .................... 433/29 |
| 6,674,530 | B2 | * | 1/2004 | Berstis ........................ 356/406 |
| 6,798,517 | B2 | * | 9/2004 | Wagner et al. ............... 356/406 |
| 7,099,732 | B2 | * | 8/2006 | Geng .......................... 700/117 |
| 2003/0035107 | A1 | | 2/2003 | Overbeck et al. ........... 356/405 |
| 2005/0003323 | A1 | * | 1/2005 | Katsuda et al. ............... 433/29 |

FOREIGN PATENT DOCUMENTS

| DE | 297 04 185 U1 | 6/1997 |
| DE | 197 09 500 C1 | 7/1998 |
| DE | 100 13 210 A1 | 9/2001 |
| WO | WO 02/43604 A2 | 6/2002 |

\* cited by examiner

*Primary Examiner*—Ralph A Lewis
(74) *Attorney, Agent, or Firm*—Marshall, Gerstein & Borun LLP

(57) ABSTRACT

In a dental device for the investigation of the optical properties of tooth tissue, in particular for the recognition of caries, plaque, bacterial infection, concretions and tartar, having a generator for generating an excitation radiation, which is to be directed onto a tooth tissue region to be investigated, a radiation detector and a radiation evaluator for the detection and evaluation of a response radiation arising from the irradiated tooth tissue region as response to the irradiation, and an indicator means for the indication of a measurement result determined by the evaluation means on the basis of the detected response radiation, the excitation radiation generator, the radiation detector and at least also the indicator being integrated in a dental handpiece.

3 Claims, 13 Drawing Sheets

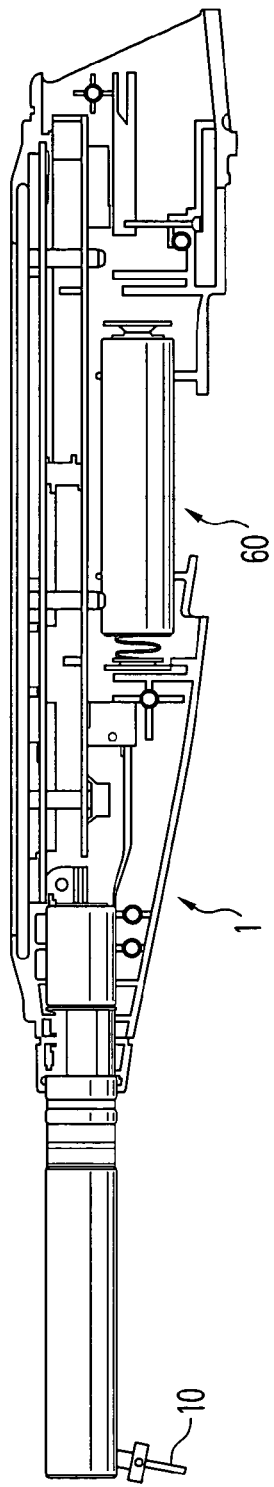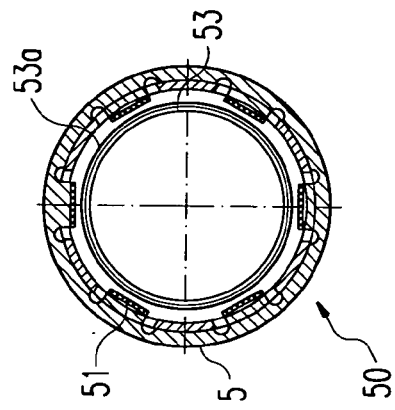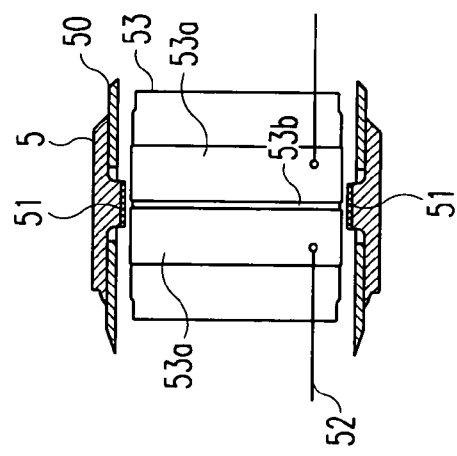
Fig. 14
Fig. 13
Fig. 12

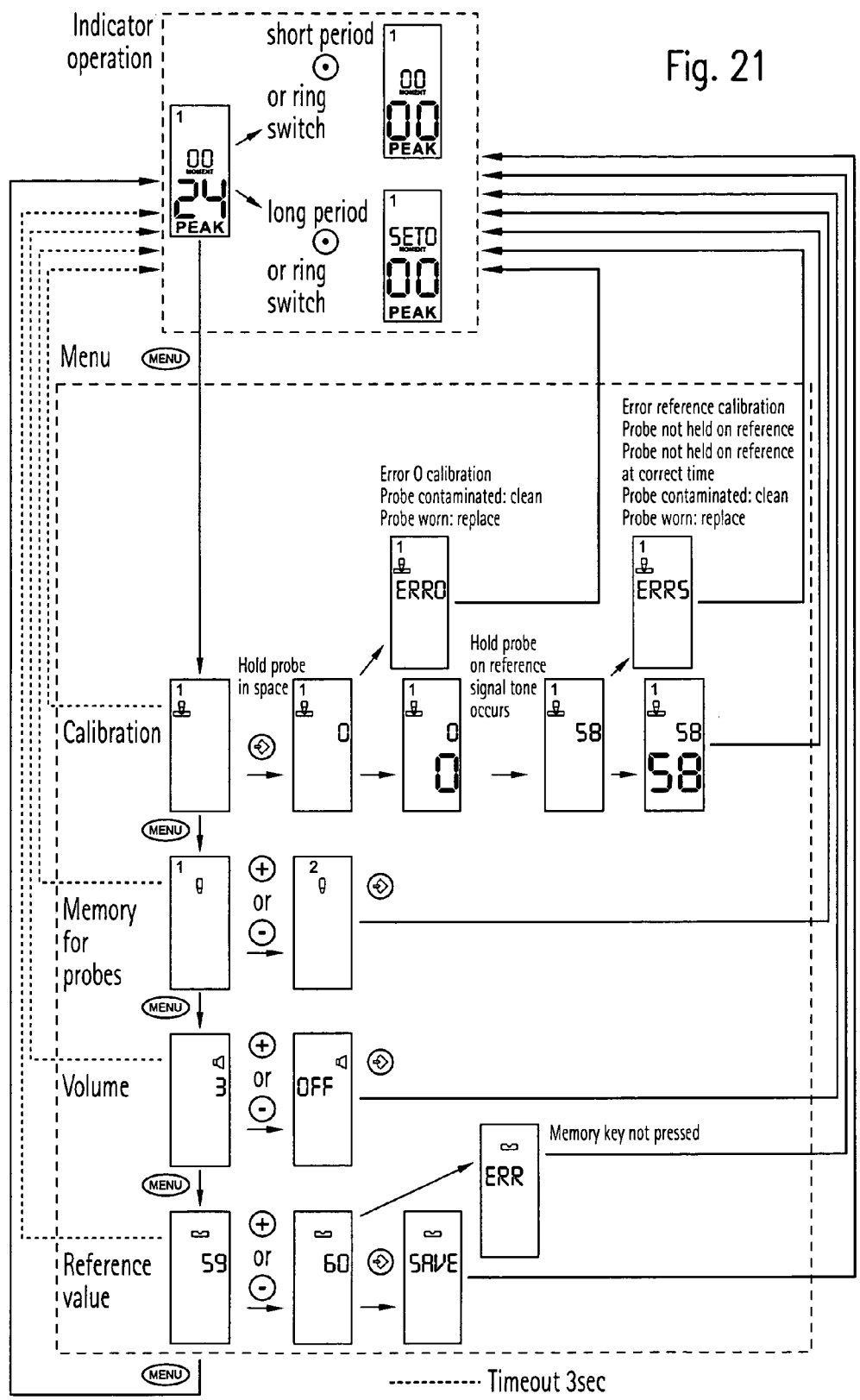

DENTAL DEVICE FOR THE INVESTIGATION OF THE OPTICAL PROPERTIES OF TOOTH TISSUE

BACKGROUND OF THE INVENTION

1. Field of the Invention

The invention relates to a dental device for the investigation of the optical properties of tooth tissue. In particular the present invention relates to a device for the detection of fluorescent substances on teeth, for example of caries, plaque, bacterial infection, concretions or tartar.

2. Related Technology

In dental diagnostics, optical investigation devices, with the aid of which for example caries, plaque, bacterial infection, concretions or tartar can be recognized, have long been known and known in different variants. It is common to all known devices that a tooth tissue region to be investigated is first irradiated with an excitation radiation, in response to which a response radiation is issued from the tooth. This response radiation may contain both the return reflected radiation of the same wavelength and also a fluorescence radiation. The response radiation is in turn detected and delivered to an evaluation unit which on the basis of the spectrum of the response radiation determines whether one of the above-mentioned substances is present or not. The known optical diagnostic methods and devices differ thereby in the employed wavelength(s) for the excitation radiation and in the evaluation of the detected response radiation. A first possibility consists in investigating whether there has arisen at the tooth a fluorescence radiation as reaction to the excitation radiation. Another possibility consists in, in the case of so-called reflection spectrometry, investigating which wavelengths are reflected in what manner from the tooth surface.

Devices of this kind are described for example in DE 297 04 185 U1, DE 197 09 500 C1 or DE 100 13 210 A1. These known devices have a dental handpiece with an investigation probe, via which the excitation radiation is directed to the tooth to be investigated and the response radiation radiated back from the tooth is detected. The light source for generating the excitation radiation is thereby often arranged directly in the handpiece, whilst in contrast the evaluation of the response radiation is mostly effected in a console, which is connected with a handpiece via a connection tube. This console has on the one hand the electronics for the control of the light source for the excitation radiation and also for the evaluation of the response radiation. Beyond this, there are provided at the console indicator means of the form of a display, which depict the measurement results and thereby provides information as to whether the region just investigated manifests one of the above-mentioned fluorescent substances or not. The final diagnosis, i.e. the determination whether the increased fluorescence is caused by caries or not, is then made by the dentist.

GENERAL DESCRIPTION OF THE INVENTION

The invention is based on an intended object of further improving the handling of dental optical investigation devices thus far known. Here it is to be taken into account that for a user of the apparatus the possibility should exist of also being able to investigate regions within the mouth of a patient that are difficult to access. Further, the possibility of a simple cleaning should be provided, since in particular those parts which enter into the mouth of a patient must also be sterilized.

In accordance with a first aspect of the invention, the dental investigation device is configured so that it is constituted by means of a hand apparatus, which in principle can be used completely independently of other equipment and comprises all elements significant and necessary for carrying out the optical diagnosis procedure. Thus, the device in accordance with the invention has an excitation radiation generator, which radiation is to be directed onto a tooth tissue to be investigated, a radiation detector and a radiation evaluator for detecting and evaluating a response radiation sent back from the irradiated tooth tissue region as response to the irradiation, and an indicator for indicating a measurement result determined by the radiation evaluator on the basis of the detected response radiation, wherein the excitation radiation generator, the radiation detector and at least also the indicator are arranged in or on a handpiece. The indicator for representing the measurement result may thereby both be of optical and also acoustic nature, and provide the user of the apparatus directly with the current measurement result. Preferably, also the radiation evaluation is integrated in the handpiece.

Through the configuration of the optical investigation device as an autonomous working handpiece, the user of the device is no longer restricted in his range of movement. The handling of the device is thus, in comparison with the known devices, in which the handpiece is connected via a supply tube with a console, significantly improved.

In accordance with an advantageous development of this inventive concept, it can be provided that the measurement results provided by the investigation device are transmitted in a wireless manner to an external depiction and/or evaluation unit, to be supplemented or further processed. This external unit may be, for example, a PC within a dental practice, in which the measurement results obtained during the investigation are automatically stored and associated with the appropriate patient. Further, this external unit may be employed for additional depiction of the measurement result—for example on the basis of a tooth schematic. The transmission of the signals may thereby take place in the form of electromagnetic signals, by means of ultrasound or other known wireless transmission techniques.

A second aspect of the invention is concerned with the problems of cleaning or sterilization of the investigation device. As has already been mentioned above, simple cleaning should be possible since high hygiene requirements arise in dental practices. Since at least the forward part of the investigation device enters into the mouth of the patient in particular there should be the possibility of sterilizing this region.

In accordance with a second aspect of the invention it is thus proposed to provide the handpiece, in which the elements of the optical investigation device are arranged, at least in its forward region, with a sleeve which is removable and is of sterilizable material. Since with this solution, solely the sleeve and the investigation probe needed for transmission of the excitation and response radiation comes into contact with the patient, after an investigation the probe and the sleeve can be removed from the handpiece and separately sterilized, whereby in particular the electronic components of the device necessary for control of the light source and evaluation of the response radiation remain in the region of the handpiece which is not to be cleaned and thereby are not affected.

In accordance with an advantageous development of this second concept in accordance with the invention, the sleeve may have parts of a switching element for activation of the device or the means for the generation of the excitation radiation. In particular, the switching element may be a ring switch which has an electrical line running in the interior of the handpiece which in the region of the ring switch is interrupted. The removable sleeve has in the region of the interruption an actuable element having a bridging element of a conductive material, via which the line can be closed and therewith the handpiece and the means for generation of the excitation radiation activated. Preferably, the actuable element is a switch cap of a flexible material.

The removable sleeve is preferably able to be put in place on the handpiece from the forward side, whereby in particular it can be provided that the sleeve can only be pushed on or removed if the diagnosis probe provided for the transmission of the excitation and response radiation is removed from the handpiece. This probe also is preferably releasably attached at the forward handpiece end, in particular latched, and may be rotatably mounted. Thereby it can further be provided that differently configured diagnosis probes are available, which in each case couple in and couple out the light of the excitation and response radiation in a particular manner corresponding to the region which is presently to be investigated. Through this the possibility is opened up of employing the investigation device in accordance with the invention e.g. both for the investigation of chewing surfaces and also for the investigation of tooth gum pockets and tooth intermediate spaces.

A third aspect of the invention concerns itself with the problem of configuring the elements necessary for detecting the response radiation sent back from the tooth surface as compactly as possible, so that these can be integrated in the handpiece is a space saving manner.

Thereby, in accordance with the third aspect of the invention, the invention provides a photodiode for the detection of the response radiation within a small housing which is emplaced in the handpiece. The transmission of the response radiation to the photodiode is thereby effected by means of a light conductor, at the one end of which the photodiode is arranged. In order to make possible an optimal coupling in of the light transmitted by the light conductor into the photodiode, the housing may thereby have an opening in which the light conductor opens, whereby on the housing in particular a snap fastening for attachment of the light conductor may be arranged. Preferably, there is provided within the housing also a filter arranged between the light conductor end and the photodiode, which only allows through the wavelengths necessary for the evaluation of the response radiation. This compact arrangement makes possible a very effective evaluation of the response radiation arising in response to the irradiation with the excitation radiation, whereby at the same time wide ranging miniturization is attained.

BRIEF DESCRIPTION OF THE DRAWINGS

Other developments and advantageous configurations of the device in accordance with the invention. They will be described in more detail in connection with the description of several exemplary embodiments of the present invention with reference to the accompanying drawings. There is shown:

FIGS. 12 and 13 a possibility for the realization of a switching element, for activation of the excitation radiation, which is simple to clean;

FIG. 14 the investigation device in accordance with the invention, in partial section;

FIG. 21 the operating and use schematic of the investigation device in accordance with the invention.

DETAILED DESCRIPTION OF THE DRAWINGS

Figure 1:
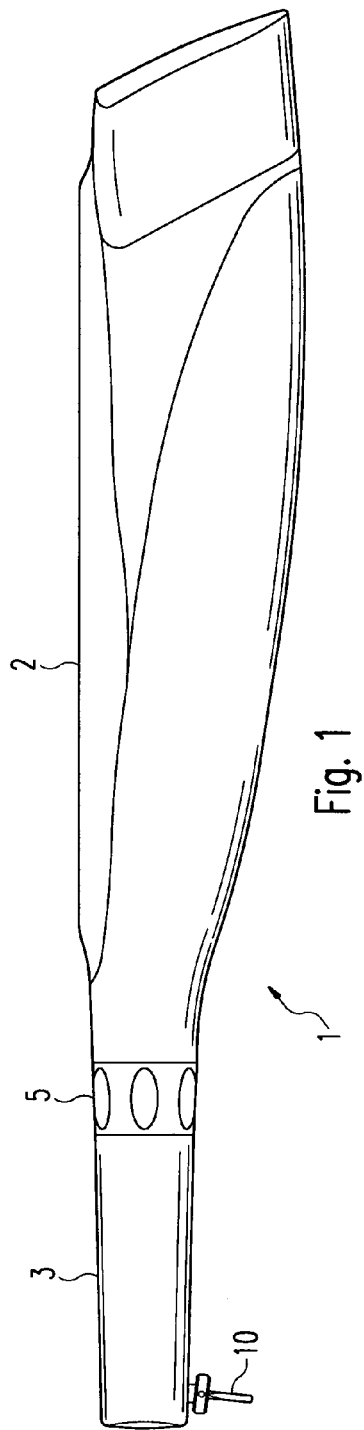
FIG. 1 a dental optical investigation device in accordance with the invention, in the form of a handpiece.

FIG. 1 shows an exterior view of a first exemplary embodiment of a dental device in accordance with the invention for the investigation of tooth tissue, in particular for the recognition of caries, plaque, bacterial infection, concretions or tartar. The device is configured as handpiece 1, which in accordance with a first inventive concept can be used entirely independently of further external consoles or evaluation and depiction units. The elongate grip body 2 has for this purpose, in its forward head region 3, a probe 10 standing to the side slightly obliquely downwardly, which is provided for the transmission of an excitation radiation onto the tissue region to be investigated and for the transmission of the response radiation radiated back from the tooth, to an evaluation unit arranged in the handpiece 1. The precise configuration and function of this probe 10 will be described in detail below.

In the forward region 3 of the handpiece 1 there is further provided a ring switch 5, which can employed for the activation of the excitation radiation source. As will likewise be explained in more detail below, this ring switch 5 is a component of a sleeve which can be removed from the handpiece 1 to the forward side, through which a simple cleaning and sterilization of those parts of the handpiece 1 which come into contact with the patient is made possible.

Figure 2A:
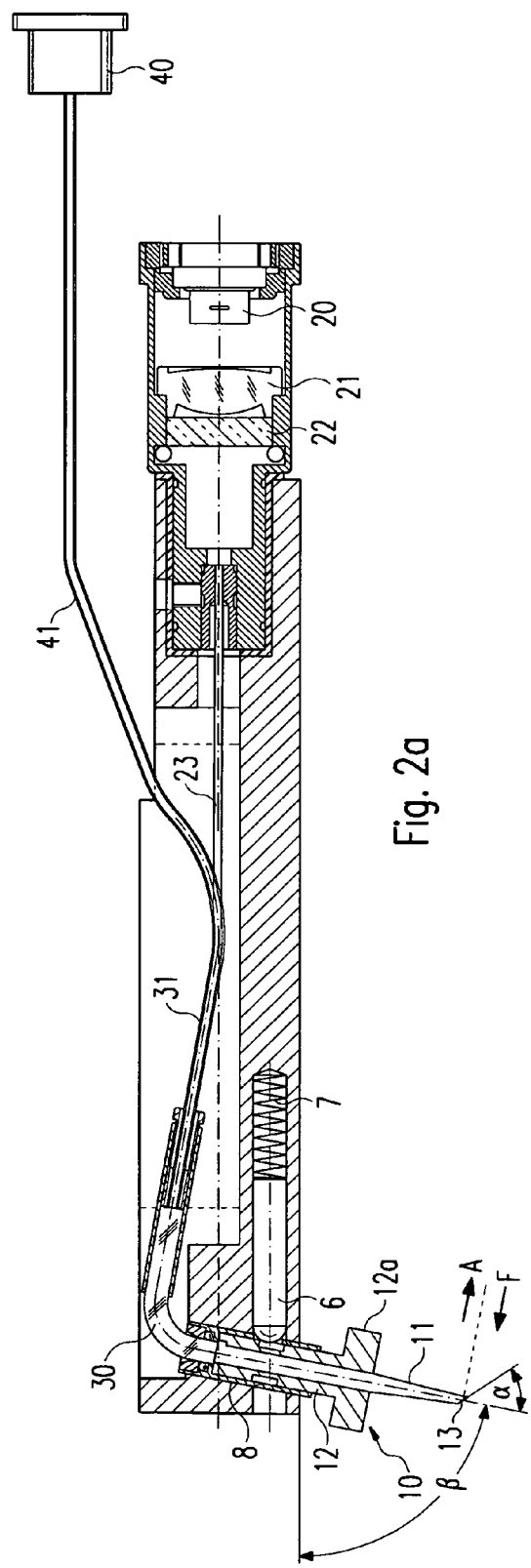
FIG. 2a the configuration and arrangement of the main components for optical diagnosis of caries.
Figure 2B:
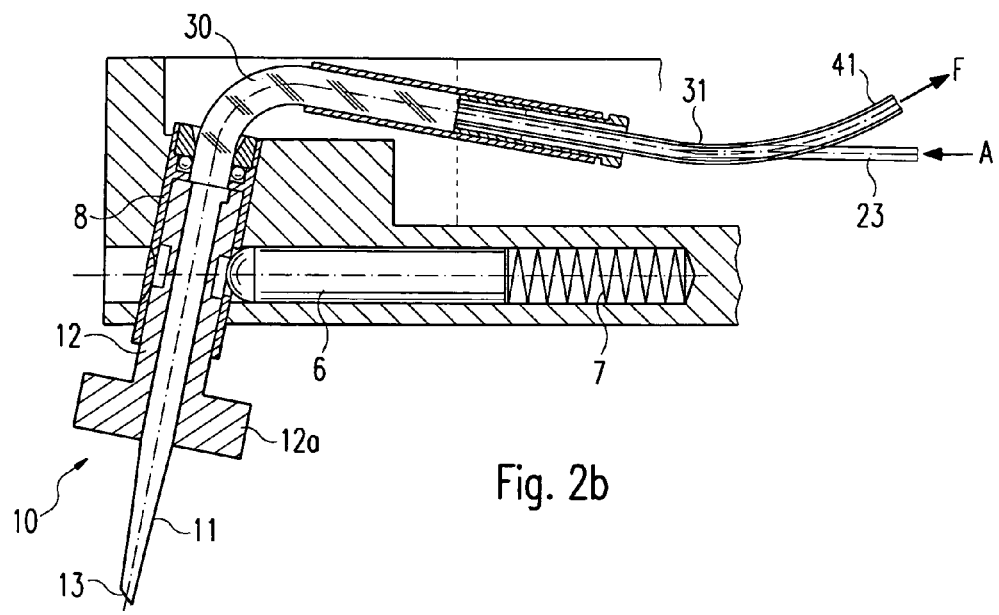
FIGS. 2b and 2c representations of FIG. 2a to an enlarged scale.
Figure 2C:
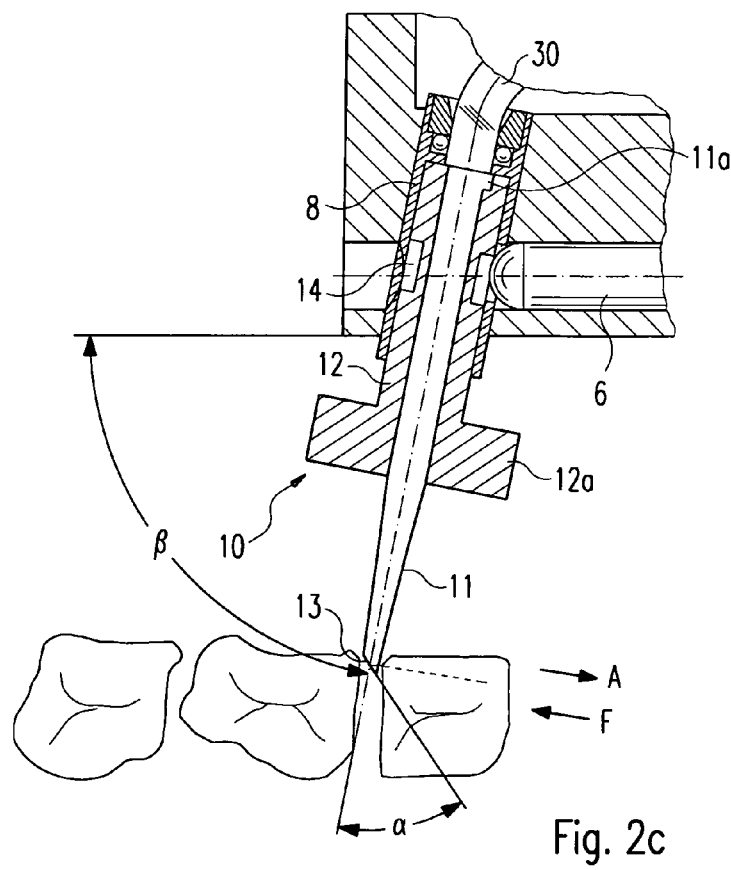

FIGS. 2a to 2c show those components of the investigation device which are required for the recognition of the abovementioned materials at an investigated tooth tissue region. As with the previously known optical investigation devices, the investigation is effected in that the tooth tissue to be investigated is exposed to an excitation radiation and the response radiation arising therefrom is detected and evaluated. The main components of the handpiece 1 are thus on the one hand a light source for the generation of the excitation radiation, evaluation means for the evaluation of the response radiation and means for transmitting the excitation radiation to the region to be investigated and for transmitting the response radiation to the evaluation means.

In the case of the illustrated handpiece 1, the light source for the generation for the excitation radiation is formed by means of a laser diode 20 which generates a virtually monochromatic light. In particular, the excitation radiation may lie in the region between 600 nm and 670 nm, in particular at ca. 655 nm, since with such a wavelength the best possible compromise between the output power of the laser diode 20 and the spectral differentiation between the excitation radiation and the response radiation sent back from the tooth surface can be attained. It is to be noted that the function of the handpiece in accordance with the invention will be explained here using the example of fluorescence diagnosis, in which the fluorescence radiation arising at the tooth surface in reaction to the irradiation is evaluated. Alternatively, thereto, there is however also the possibility of using other wavelengths for the excitation and/or response radiation, or to investigate, in the scope of a so-called reflection spectrometry, which wavelengths are reflected from the tooth surface in what manner.

With the aid of a lens 21 arranged before the laser diode 20, and an optical filter 22 which further restricts the light emitted from the laser diode 20 to the desired wavelength region, an excitation radiation A is then generated and coupled into a first light conductor 23. This light conductor 23 may be an individual light fibre having a diameter of ca. 0.5 mm; however there is also the possibility of forming the light conductor 23 from a plurality of individual light conductor fibres. At its forward end the light conductor 23 borders on a curved fibre rod 30, of a likewise light conducting material, through which the excitation radiation is deflected and coupled into the end face of the diagnosis probe 10.

Figure 3:
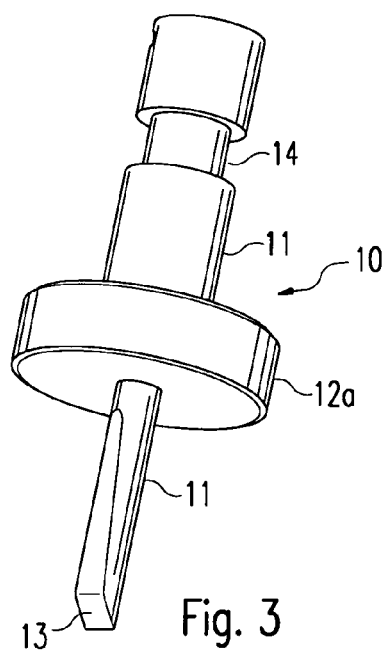
FIG. 3 a representation to an enlarged scale of a first exemplary embodiment of a diagnosis probe for the transmission of the excitation and response radiation.

The precise configuration of the diagnosis probe 10 can be understood from the perspective representation in FIG. 3. Here there is involved a probe for the investigation of tooth intermediate spaces. The significant element of the probe 10 is an elongate light wedge 11 of a transparent material, at the lower end of which the excitation radiation A is coupled out and directed onto the tooth region to be investigated. As material for the light wedge 11 there can be employed for example plastic or sapphire, whereby plastic is advantageous with regard to the lesser danger of breakage and lesser production costs, but however has disadvantages with regard to manifestations of wear and the working life resulting therefrom.

As can be understood in particular from the illustration in FIG. 2c, the light is to be coupled out laterally of the longitudinal axis of the light wedge 11, in order to make possible an investigation of the tooth intermediate spaces. For this purpose, the forward end of the light wedge 11, which is of a transparent material, is provided with a bevel 13 which includes with the longitudinal axis of the light wedge an angle α of ca. 40 to 45°. The light incident from above is then totally reflected at the bevel 13 and coupled out of the light wedge 11 to the side. Additionally or alternatively, the bevel 13 may be mirrored, in order to attain the deflection of the light.

The return transmission of the response radiation F, arising at the tooth surface due to the irradiation, is effected in similar manner in the reverse direction. First, the response radiation falls laterally into the light wedge 11 and is again reflected at the bevel 13 and thus directed to the end face of the probe 10 and coupled into the fibre rod 30. From the end of the fibre rod 30, which in turn is preferably of a plurality of individual fibres having a diameter of 0.1 mm and has overall a diameter of ca. 1.4 mm, the response radiation is then coupled into a light fibre bundle 31, which on the one hand is of the excitation radiation fibre or fibres 23 for the excitation radiation A and on the other hand is of a detection fibre 41 for the transmission of the response radiation F.

Via the detection fibre 41, which preferably has a diameter of 0.25 mm, there is effected the passing on to a detection device 40, the detailed construction of which will be described below. The task of this detection device 40 is to detect the response radiation radiated back from the tooth surface, to analyze the response radiation and on the basis of the measurement result to determine whether one of the fluorescent substances mentioned above is present at the investigated tooth surface or not.

With regard to the diagnosis probe 10 it is to be remarked that this is mounted rotatably by 360° in the head region 3 of the handpiece 1 so that the handpiece 1 can be brought to the tooth to be investigated in a very flexible manner. The probe 10 is thereby latched with the head region 3 of the handpiece 1 and can be removed in a very simple manner—e.g. for purposes of cleaning or for replacement by another probe. For this purpose there are provided in the head region 3 of the handpiece 1 first a cylinder shaped guide 8 for the probe 10 and a latching pin 6, which with the aid of a spring 7 presses against the probe 10 and therewith holds this in the emplaced position within the guide 8. The forward ball segment of the latch pin 6 thereby engages into a circumferential recess 14 of a holder 12 for the light wedge 11, so that the probe 10 is always pressed into contact and is mounted securely within the handpiece 1 but at the same time rotatably. A rotation of the probe 12 by hand is thereby facilitated by means of a disk or ring shaped annex 12a on the holder 12, which with the fingers can readily be grasped and rotated by a user of the handpiece 1. The holder 12 itself has an elongate bore, in which the light wedge 111 is emplaced, whereby the possibility arises of exchanging the light wedge 11. A defined arrangement or orientation of the light wedge 11 within the holder 12 is ensured by means of a nose 11a, which cooperates with a corresponding recess in the holder 12.

It is further to be remarked that with respect to the handpiece longitudinal axis the diagnosis probe 10 is held not at a right angle, but preferably slightly obliquely at an angle β of ca. 80°. It has been found that through this a particularly ergonomically favourable handling of the investigation device in accordance with the invention is attained.

The releasable holding of the probe 10 on the one hand provides the advantage that the probe 10, after each investigation, can be removed and cleaned and disinfected separately from the remaining components of the handpiece 1. On the other hand, there is however also the advantage that the probe 10 can be easily exchanged and replaced by a differently configured probe. Through this there is the possibility of making available differently formed probes, which can be configured in dependence upon the location or surface configuration of the tooth site to be investigated.

Figure 4:
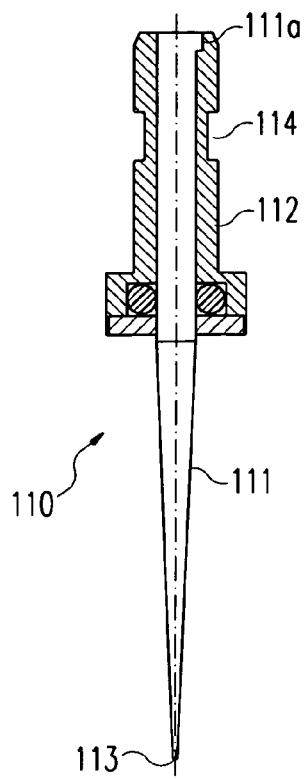
FIG. 4 a second variant of a diagnosis probe, in section.
Figure 5:
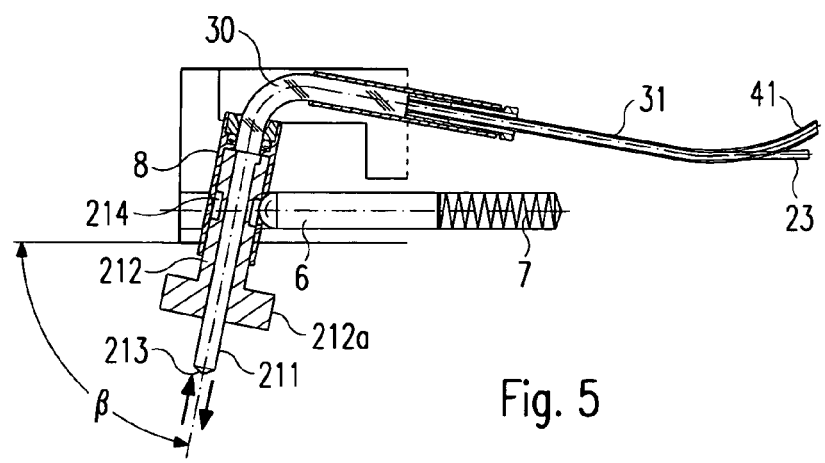
FIG. 5 a third variant of a diagnosis probe.

FIGS. 4 and 5 shown by way of example two further probes which find employment with the diagnosis system in accordance with the invention. In the case of the probe 110 illustrated in FIG. 4 there is involved a so-called paroprobe which is provided for the investigation of tooth gum pockets and in particular for the localization of subgingival concretions at tooth roots. In contrast to the probe 10 illustrated in the preceding Figures, which is for investigation of the approximal area or tooth intermediate area, the paroprobe 110 has no bevel at the probe tip, but is solely flattened off straight at the extreme end. Through this there is attained a very slim light exit with a small diameter, so that the excitation radiation can be directed in a very concentrated manner onto a site to be investigated. In contrast, a light exit at the periphery of the probe 110 is not provided. Thus, the paroprobe 110 is again of an elongate light wedge 111 of a light conducting material having a forward light exit tip 113, wherein the light wedge 111 is held by means of a holder 112 having a disk-like annex 112a, which has in the rearward region again the peripheral recess 114, via which a latching with the handpiece is attained.

A third probe 210 for carrying out of investigations in the region of fissures—that is for investigation of the chewing surfaces of teeth or of smooth surfaces or tooth outer surfaces—is illustrated in FIG. 5. The central element of this third probe 210 is a cylinder-shaped light rod 211 which has in its forward end region a truncated cone shaped end 213, via which the light is issued in the longitudinal direction of the probe 210 and coupled in the reverse direction. Also this third probe has the recess 214 required for releasable latching with the handpiece 1, and the holder 212 with the disk-shaped annex 212a. It is to be remarked however, that in the case of the probes of FIGS. 4 and 5, rotatability is not necessarily required since a light exit or light entry occurs any event always in the direction of the longitudinal axis of the probe 110 or 210.

Figure 6:
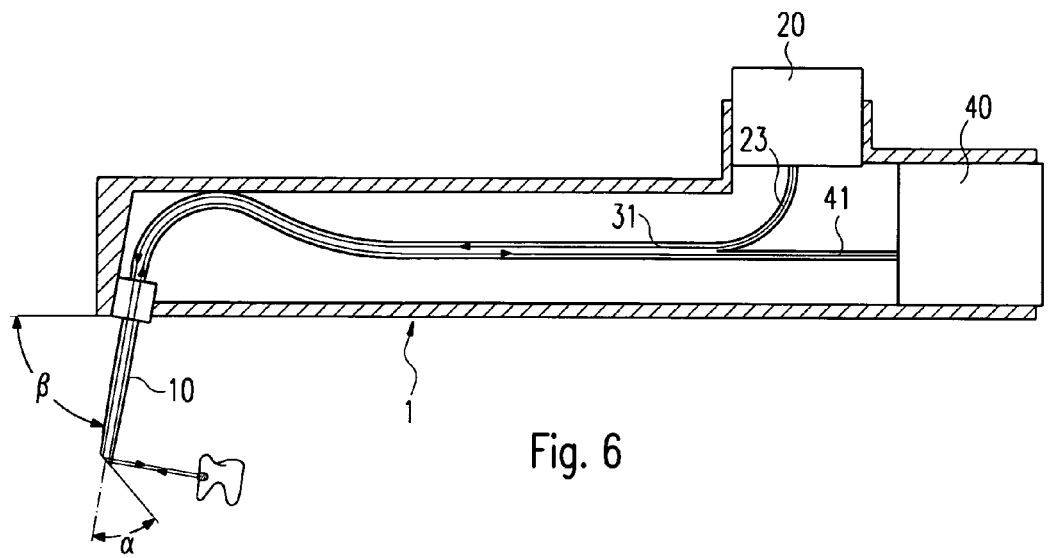
FIG. 6 a schematic of the transmission of the excitation and response radiation in accordance with a first exemplary embodiment.

In the case of the exemplary embodiment illustrated in FIGS. 2a to 2c, the transmission of the excitation and response radiation A and F was effected in the forward end region of the handpiece 1 with the aid of a curved fiber rod 30, at the handpiece side end of which there adjoin the various light conductor bundles 23 or 41 for the excitation radiation and response radiation. As illustrated in FIG. 6, there is however also the possibility of going without this fiber rod 30 and instead of this bringing together the two bundles 23 for the excitation radiation and 41 for the response radiation to a common fiber bundle 31, which extends up into the end region of the probe 10 and directly couples light in and light out of this. The common fiber bundle 31 is thus on the one hand of fibers for the transmission of the excitation radiation A and on the other hand of fibers for the transmission of the response radiation F. In particular it can be provided to arrange the fibers for the excitation radiation A centrally and to surround them concentrically with the fibers for the response radiation F.

Figure 7:
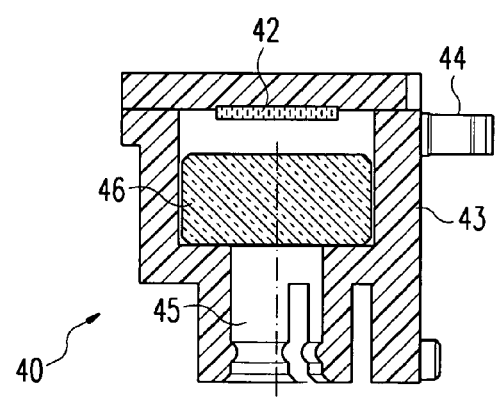
FIG. 7 a representation of an arrangement and configuration of the photodiode provided for the evaluation for the response radiation in accordance with the invention.

In the case of the exemplary embodiment of FIGS. 2a to 2c and also in the case of the variant illustrated in FIG. 6, a light conductor 41 however opens into a device 40 for the detection of the response radiation, the more detailed configuration of which will now be described with reference to FIG. 7.

The main element of the detection unit 40 is thereby a photodiode 42, which detects the response radiation F and transforms it into an electrical signal corresponding to the intensity of the response radiation F. The amplitude of the intensity of the response radiation F then provides an indication of whether, at the investigated tooth tissue region, fluorescent materials are present or not.

Since this photodiode 42, or the silicon chip responsible for transforming the incident response radiation into an electrical signal, is a relatively sensitive component this should be protected as well as possible from external influences and vibrations. In accordance with the preferred exemplary embodiment illustrated in FIG. 7, the photodiode 42 is thus integrated in a housing 43 which is arranged as a whole in the handpiece 1. A pin 44 standing to the side from the housing 43 serves for latching on a board within the handpiece 1.

So that the light of the response radiation F transmitted through the fiber bundle 41 can be evaluated as effectively as possible, it is necessary to direct the light as exactly as possible on to the photodiode 42. In order to ensure this, there is provided in the forward end of the housing 43 a cylinder-like opening 45, into which the light conductor bundle is inserted. By means of the opening 45, the bundle is so held that the light is directly directed on to the photodiode 42. Beyond this, a snap fastening is provided in the opening 45, by means of which the fiber bundle 41 is also held fast in the desired position. Finally, there is integrated in the housing 43 further a filter 46, which filters out wavelength regions not relevant for the evaluation of the response radiation F. It is thus ensured that by means of the photodiode 42 only such light is detected and evaluated which is also relevant for the diagnosis of fluorescent material. With the above-mentioned example of fluorescent diagnostics with an excitation wavelength of ca. 655 mm, the filter 46 is for example so configured that solely radiation with wavelengths above 680 mm is allowed to pass. The arrangement illustrated in FIG. 7 is thus not only extremely compact but also at the same time ensures an evaluation of the response radiation F which is as effective and exact as possible.

Figure 8:
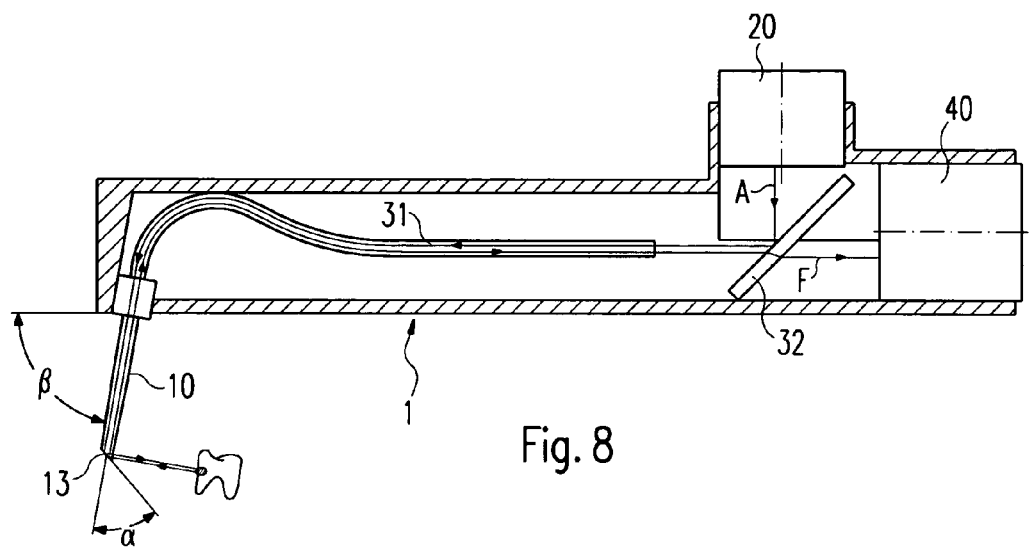
FIGS. 8 and 9 two further possibilities for the transmission of the excitation and response radiation.
Figure 9:
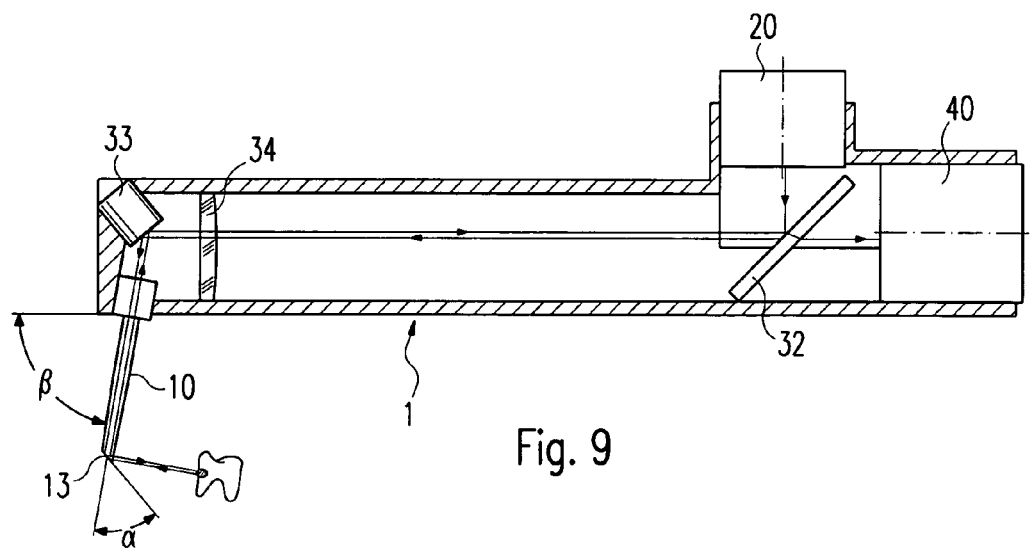

FIGS. 8 and 9 show, supplementing FIGS. 2a-c and 7, two further variants for the transmission of excitation and response radiation. Thereby, in the case of the variant according to FIG. 8 there is in turn provided initially a fiber bundle 31, which is provided both for the transmission of the excitation and also the response radiation. However, the fiber bundle 31 is not then split itself into two separate bundles for the different radiations, but is with its rearward end directed at a dividing mirror 32 or beam divider, which is partially transparent and is responsible for the coupling in and coupling out of the excitation and response radiation. The dividing mirror 32, arranged inclined with respect to the optical axis of the rearward end of the fiber bundle 31, is thereby of a material which on the one hand reflects the excitation radiation A originating from the photodiode 20 and on the other hand lets through the interesting response radiation F in the direction of the detection unit 40, as far as possible unhindered. Of course, the position of the photodiode 20 and the detection unit 40 can be exchanged, insofar as the divider mirror 32 is correspondingly coated, that is transparent and reflecting in suitable manner for the appropriate wavelengths.

In contrast, in the case of the variant according to FIG. 9, a common fiber bundle for the transmission of the radiation is completely omitted and instead the light of the excitation and response radiation directed with the aid of mirrors and lenses towards the probe and in the reverse direction. The fiber bundle 31 provided in the variant of FIG. 8 is hereby replaced by means of a deflection mirror 33 in the head region of the handpiece 1, which deflects the light in suitable manner. With the aid of a focusing lense 34, likewise arranged in the head region, it is ensured that the light is also incident in a desired bundled manner on the various optical elements. The coupling in and coupling out of the excitation and response radiation is effected in turn with the aid of the divider mirror 32 arranged in the rearward region of the handpiece.

As already mentioned in the introduction, in the case of investigation devices which come into contact with a patient, it is of greatest importance that these can also be effectively cleaned and sterilized. Since in accordance with the present invention all components of the investigation device are arranged in the handpiece 1, there arises the difficulty that the electronic components for control and evaluation of the response radiation may not be exposed to demands which are too great. Since in the case of hot air sterilization methods, which commonly come into use, the electronic components could be damaged, measures must be taken in which this is prevented.

The solution to this problem in accordance with the invention consists in providing the handpiece 1 with a sleeve, which can be removed from the handpiece and separately sterilized, whereby the sleeve itself is that part with which the patient comes into contact and which contains as few electronic components as possible. This solution will now be explained in more detail with reference to FIGS. 10 to 13.

Figure 10:
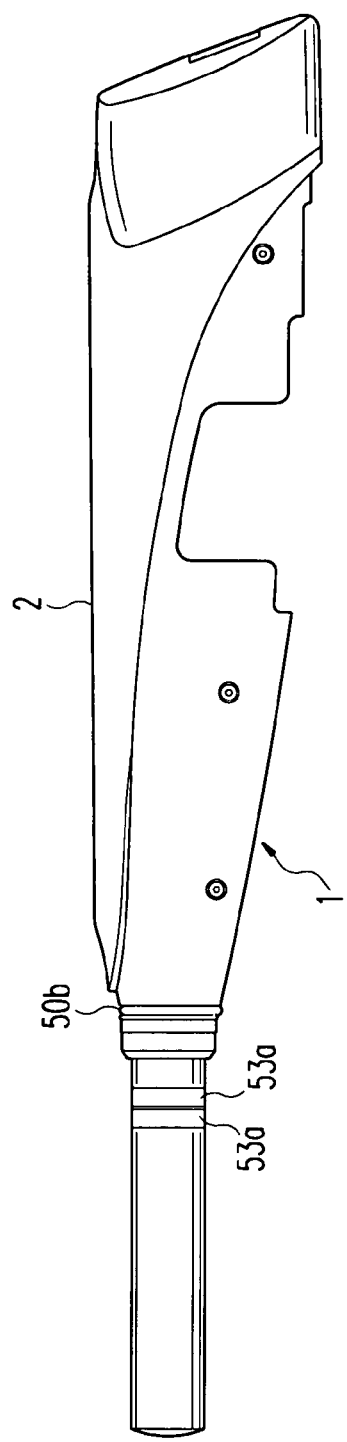
FIG. 10 the handpiece with removed sleeve.
Figure 11:
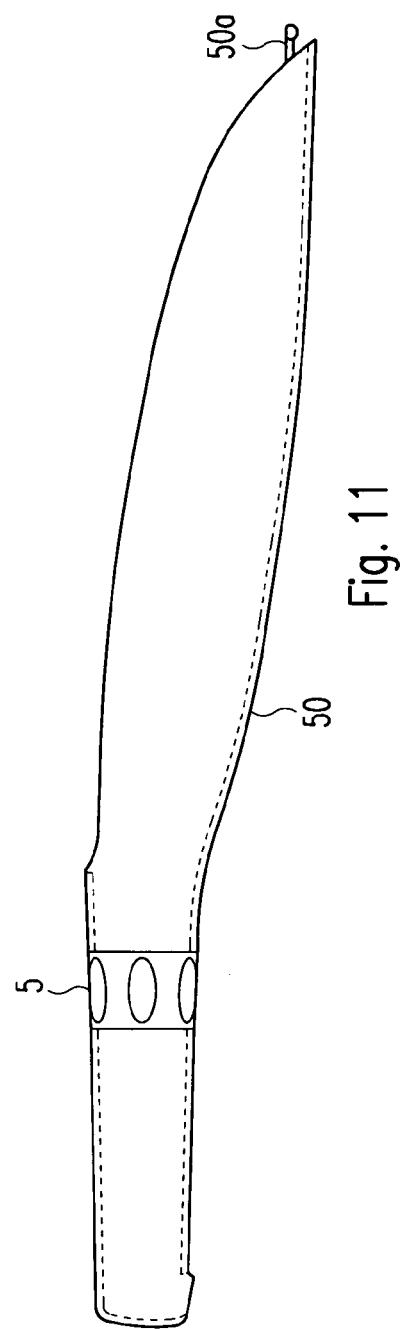
FIG. 11 the sleeve which is removable from the handpiece.

FIG. 10 thereby shows the handpiece with the already removed sleeve 50, which is illustrated in FIG. 11 in the removed condition. The sleeve 50 thereby surrounds in particular the forward end region of the handpiece 1 completely, so that it is ensured that only the sleeve 50 comes into contact with the patient, not however the inner components of the investigation device. As soon as the diagnosis probe is removed from the handpiece 1, the sleeve 50 can be taken off or pushed on onto the handpiece body 2 from the forward side, whereby with the aid of a latching pin 50a at the reward end of the sleeve 50 a secure hold between the sleeve 50 and the handpiece body 2 is attained. The hold between the two elements is further improved by means of an O-ring 50b which is arranged in the middle region of the handpiece body 2 and beyond this also provides for a sealing of the rearward handpiece region.

It is of significance that the sleeve 50 is of a material which is simple to clean and to sterilize. Further, the main electronic components of the handpiece 1 in accordance with the invention—as already mentioned—are not arranged in the sleeve 50 but in the remaining region of the handpiece 1, which does not need to be sterilized.

Since the handpiece 1 during use is, however, largely held by the fingers of the user in its forward region, the possibility is to provided of activating the light source for the excitation radiation in a manner which is favourable when gripping the handpiece, and therewith to be able to start the investigation without having to alter the grip for this purpose. Correspondingly there is provided a ring switch 5, which can be actuated also with the sleeve 50 in place, and nonetheless is not damaged by the sterilization process. The configuration of the ring switch in accordance with the invention is illustrated in more detail in FIGS. 12 and 13.

In substance, the switch is of two components, which on the one hand are arranged on or in the sleeve 50 and on the other hand in the interior of the handpiece. The substantive component of the switch in the interior space of the handpiece 1 is an electrical line 52, which is interrupted at the location of the ring switch. The lines hereby end in each case on a cylinder shaped plastic sleeve 53 which has two peripheral conductor paths 53a (which are also illustrated in FIG. 10) arranged spaced one from the other, which are separated from one another by a gap 53b. Through the making of an electrical contact between the two conductor paths 53a, the line 52 can be closed and thus an activation signal for the investigation device generated. For this purpose there are provided in the sleeve 50 a plurality of plate-like contacts 51, which are components of a switching cap in the form of a flexible ring 5, which is a component of the sleeve 50 and in the emplaced condition of the sleeve 50 on the handpiece 1 is arranged in the region of the conductor path 53a. By means of a pressing together of the ring region 5 of the sleeve 50, at least one contacting element is thus pressed on the two conductor paths 53a and establishes the electrical employment, through which then the investigation device is activated.

Instead of the separate contact pellets 51, applied to the inner side of the sleeve 50 as illustrated in FIGS. 12 and 13, there is also the possibility of integrating conducting elements into the sleeve 50 of an insulating material, for example to vulcanize them in. As a suitable material for this purpose for example carbon suggests itself, which can be worked in either in the form of individual contacting regions or as a ring-like contacting structure in the sleeve 50. Further, it would also be conceivable to form the sleeve 50 at least in the region of the ring switch 5 completely of a flexible but conductive material.

Of significance in the case of the configuration according to the invention is that solely the contacting elements 51 together with the sleeve 50 need to be sterilized. These can however be of a material which is relatively insensitive with regard to the high temperatures of a hot air sterilization, so that there is thus obtained a switching element for the activation of the investigation device which nonetheless is well sterilizable. The further components of the switch and of the investigation device overall must, in contrast, not be sterilized, so that a damage to these is avoided.

Figure 15:
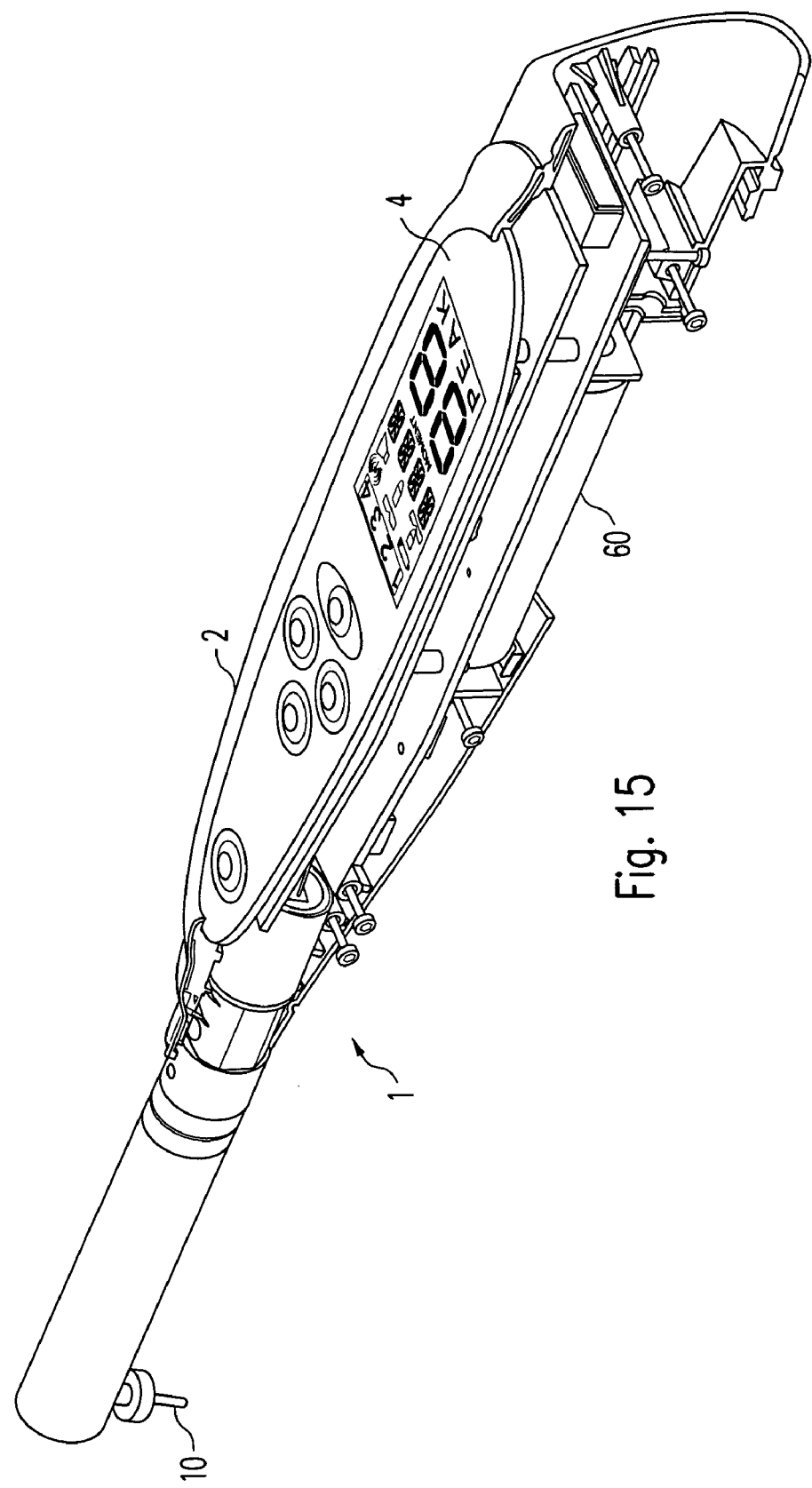
FIG. 15 the investigation device in a further perspective representation.

FIGS. 14 and 15 show the handpiece in accordance with the invention in a side or perspective illustration in partial section. As can be understood from the representations, there is provided in the rearward region of the handpiece body a battery receptacle for the current supply of the investigation device in accordance with the invention. At the upper end of the rearward region of the handpiece body 2 there is further located an operating and indication field 4, which will be further explained below. The handpiece 1 further has also a loud speaker, via which the current measurement result can be acoustically indicated. For example, with this, the intensity of the measured response radiation could be represented by a signal changing in frequency and/or in volume.

Figure 16:
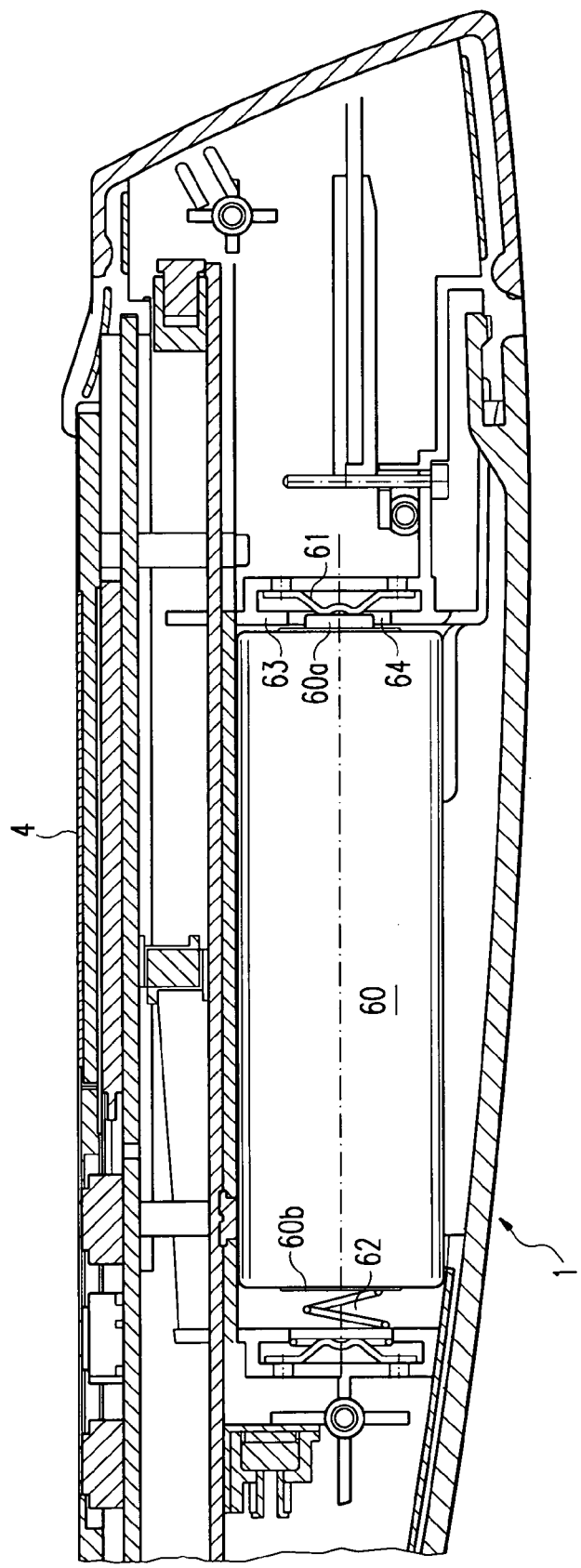
FIG. 16 the arrangement within the handpiece of a battery provided for current supply of the device.

The receptacle for the battery 60 or batteries for current supply is so configured that an unintended reversed placing of the batteries 60 is prevented. This protection against reversed polarity is illustrated in FIG. 16 and has as significant element in that region which is provided for contacting of the positive pole 60a of the battery 60 a bearing surface 63 which contains a circular recess 64. The positive pole 60a can engage through this recess and contact the terminal 61. If, however, the battery was put in place in the reverse direction, no contact would come about, since the negative terminal 60b of the battery 60 cannot engage through the opening 64 of the bearing surface 63. Damage to the apparatus through false emplacing of the battery 60 in the handpiece 1 is thus excluded. Contacting of the negative terminal 60b of the battery 60 is effected via a further contact 62 in the forward region of the handpiece.

As mentioned in the introduction, a significant feature of the handpiece 1 in accordance with the invention is that this can be employed completely independently of external equipment. All elements necessary for the carrying out of the investigation and indication of the investigation results are arranged within the handpiece 1. In particular also the indication of the measurement result, as will be explained in more detail below, is effected via the handpiece 1 itself.

Figure 17:
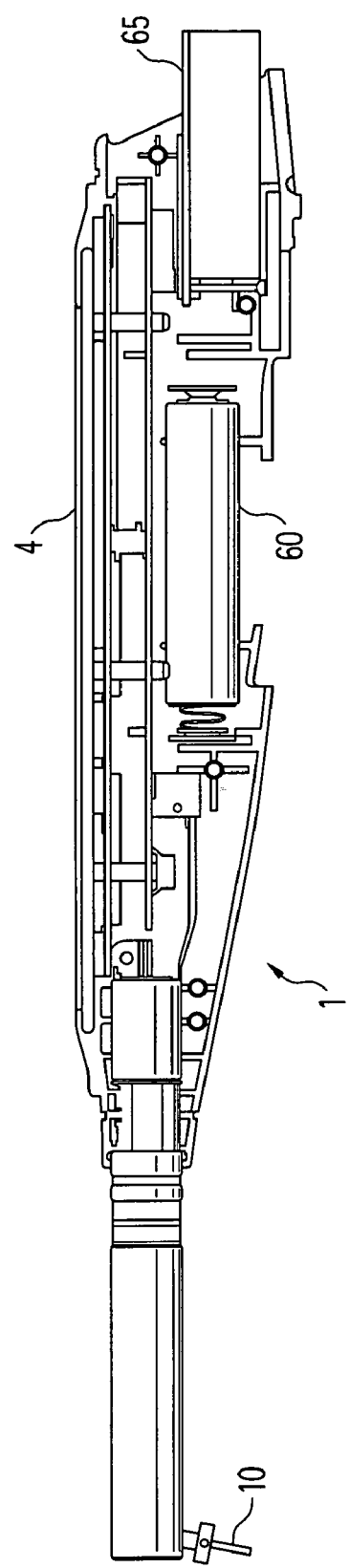
FIGS. 17 and 18 two illustrations of further variants of the device in accordance with the invention, with which there is additionally provided a radio module for wireless transmission of measurement data.
Figure 18:
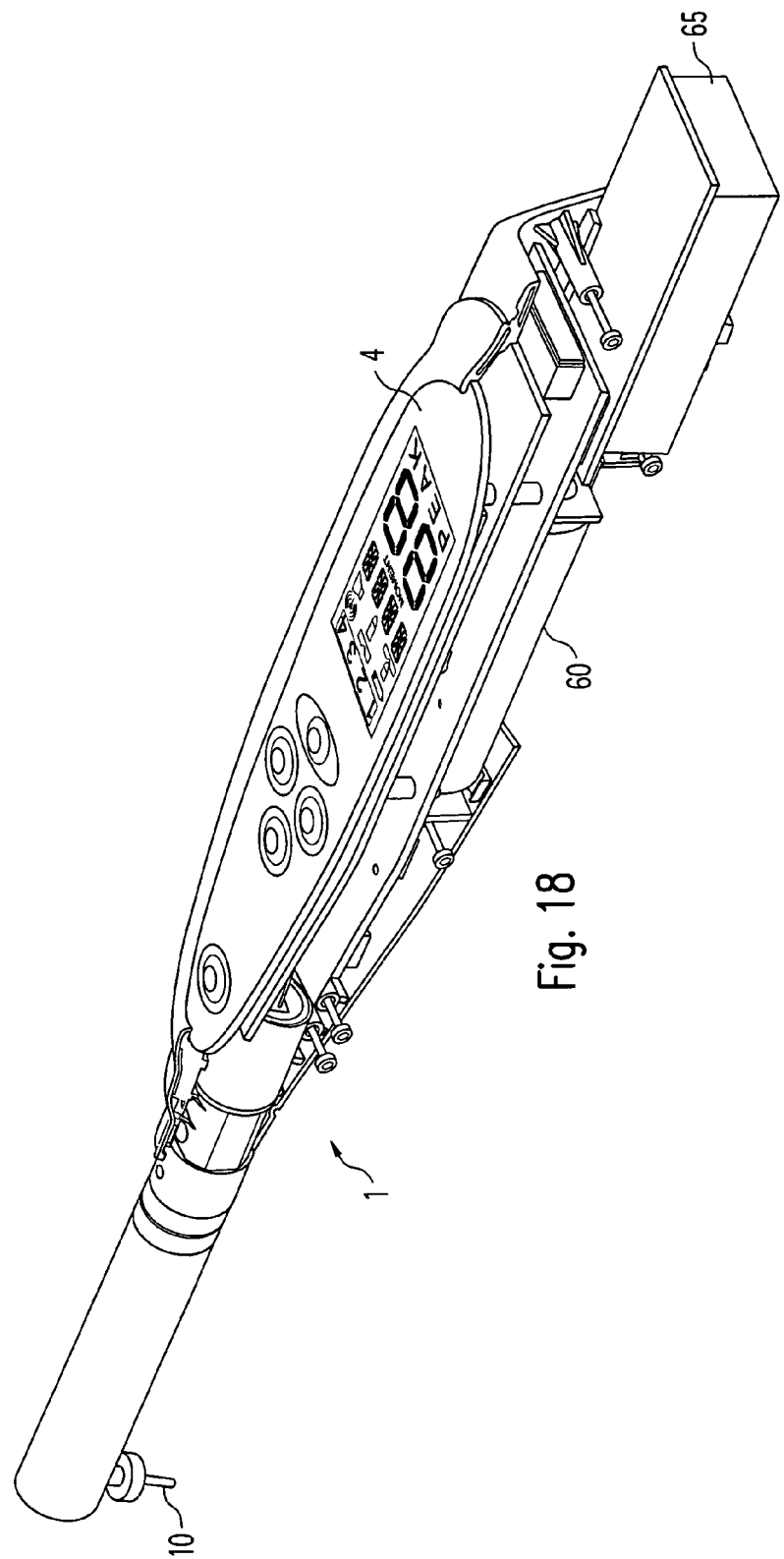

On occasion, there is however, also the need to pass on the measurement results obtained during an investigation to a central computer of a dental practice in which the measurement data is directly stored or at which an additional representation of the measurement result is effected. With the handpiece 1 illustrated in FIGS. 17 and 18 there is thus arranged in the rearward region of the handpiece 1 a communications module 65, via which the measurement data can be transmitted to an external unit in a wireless manner. The module 65 may thereby in particular be provided to transfer the measurement data as radio data, which brings with it the advantage that a high transmission quality is ensured and thus the danger of faulty transmission is virtually excluded. Alternatively thereto, however, there is also the possibility of transmitting the data by means of infrared or ultrasound signals. Both solutions can be realized very economically, but have in comparison to radio transmission only a short range. This may, however, in some circumstances even be desired, when it is to be avoided that disruptions arise between two apparatuses arranged in neighbouring rooms.

A particular advantage of the transmission of the data by means of ultrasound lies in that the loud speaker provided in the handpiece 1, which is primarily used to indicate the measurement results, can be employed at the same time also for data transfer. This means that an additional element for data transfer can be omitted and solely a suitable control of the loud speaker is to be provided.

Figure 19:
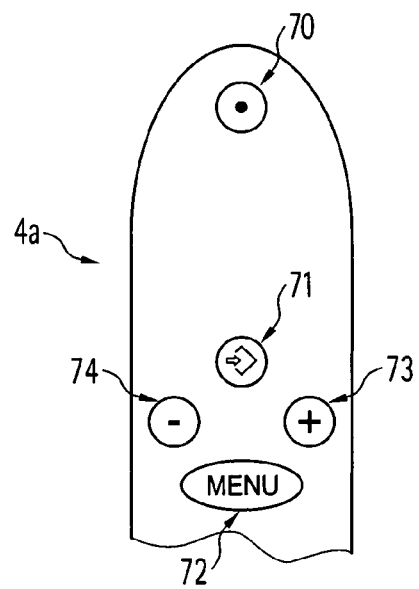
FIG. 19 an operating field provided on the handpiece for the activation or setting of the various functions.
Figure 20:
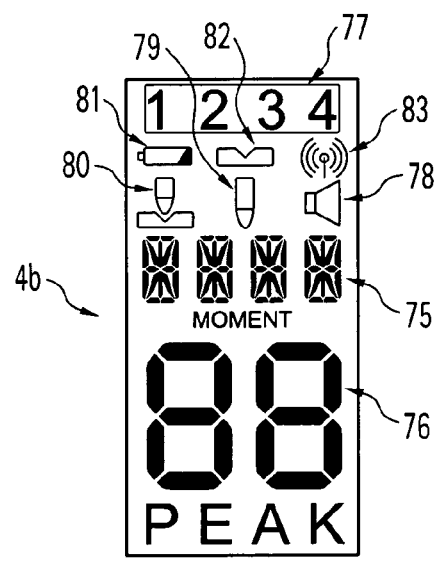
FIG. 20 the indicator provided on the handpiece for the representation of functions and measurement results.

With reference to FIGS. 19 and 21, there will be described in more detail the various functions of the investigation device in accordance with the invention and the representation and indication of the measurement result. FIGS. 19 and 20 thereby show the operating field 4a located on the upper side of the handpiece 1 for the activation of certain functions and the indicator unit 4b for the depiction of the current function or the measurement result, whilst in contrast FIG. 21 schematically illustrates the concept of user operation for the handpiece 1 in accordance with the invention.

The operating field 4a consists of in total five keys, namely a central key 70, a memory key 71, a menu key 72 and two selection keys 73 and 74. The function of the individual keys will be explained below with reference to the operating schematic of FIG. 21. The indicator field 4b has on the one hand a further digital indication 75 for depiction of the momentary measurement value, a second indicator 76 for depiction of a maximum value and an indicator 77 for the depiction of the number of the probe being used. Further, six illuminated symbols 78 to 83 are provided by means of which the status in which the handpiece 1 is at present to be found, or an action which is presently carried out, is indicated.

With the aid of the central or multifunctional key 70, on the one hand the handpiece 1 can be completely switched on and off; beyond this the maximum value can be reset or an offset correction carried out.

The function of the memory key 71, in contrast, depends upon whether or not the menu mode is active or not. In the case that the menu is at the moment not activated, through pressing of the memory key 71 a transmission of the current peak value to the central computer unit via the wireless connection is initiated, which is made apparent through the illumination of the light symbol 83. If, in contrast the handpiece 1 is at the moment in a particular menu point, through pressing of the memory key 71 the actual set value is stored and the menu exited.

Also the function of the two selection keys 73 and 74 depends upon whether the menu is active or not at the moment. In the case of inactive menu a signal can be sent to a central indication unit via the wireless connection which causes a forward movement in a tooth schematic represented on a display. In the similar manner, with non-active menu with the aid of the key 74 a reverse movement in the tooth schematic can be brought about, so that in the case of keys 73 and 74 in this situation they are used as navigation keys. In contrast, in the case of activated menu, with the keys 73 and 74 the current numerical value of the parameter to be set in the corresponding menu point can be increased or decreased.

Finally, the menu key 72 serves to call up a particular menu point, whereby selection can be made from amongst the various points in a rotating manner. The various menu points are calibration, probe selection, volume, reference value and indicator operation, whereby the various functions of these menu points can be understood from the schematic in FIG. 21.

The menu point "calibration" serves to carry out a calibration of the investigation device. After a pressing of the memory key 71 for this purpose there is first taken a null signal, which is obtained when the measurement probe is directed into free space. Then the probe is to be directed to a reference body, and a further measurement is carried out, whereby the measurement result hereby obtained is drawn upon for calibration of the investigation device.

The menu point "probe selection" can be employed to associate with the currently mounted probe a certain number. This is helpful in the case of a later evaluation of the measurement result, since each measurement result is associated with a particular probe.

The third menu point "volume" serves to set the volume of the measurement signal issued via the loud speaker. With the aid of the menu point "reference value" a reference value can finally be determined which indicates from which intensity of the measurement signal the presence of caries is determined upon, or an acoustic indication of the measurement result takes place.

In the normal operational condition, the device in accordance with the invention is in so-called indicator operation. Hereby, there is depicted in the momentary value indicator 75, upon activation of the light source for the excitation radiation, the momentary measurement value, which gives information about the intensity of the detected response radiation. At the same time there is represented in the peak value indicator 76 the peak value of the current measurement, which is determined by means of permanent comparison with the current measurement values. The storage of this peak value is of advantage because through this at a later time point of the measurement that location can again be found in a simple manner at which the greatest collection of a fluorescent substance is diagnosed.

In the indicator operation there is further the possibility, by means of a long pressing of the multifunctional key 71, of carrying out an offset correction, that is to newly set the current null value. Through a short pressing of the multifunction key, in contrast, the peak value is reset to the value null and therewith a new measurement started.

The user schematic in accordance with the invention is particularly neat and understandable, since there is involved a unitary operating schematic for each individual menu point. The operation of the investigation device in accordance with the invention can thus, after only a short time, be carried out even by inexperienced persons.

Overall there is thus indicated by means of the present invention an investigation apparatus for investigation of tooth surfaces which distinguishes itself through a particularly simply handling, at the same time however complying with the requirements for sufficient hygiene.

The invention claimed is:

1. Dental device for the investigation of the optical properties of tooth tissue, comprising
    an excitation radiation generator, which radiation is to be directed through a first light conductor,
    a diagnosis probe arranged at a forward end of the first light conductor, the probe having an elongate light wedge at a lower end of the probe, the wedge to direct the radiation onto a tooth tissue region to be investigated,
    a radiation detector and a radiation evaluator for the detection and evaluation of a response radiation arising from the irradiated tooth tissue region as response to the irradiation, the response radiation being transmitted from the irradiated tooth tissue through the elongate light wedge to an end face of the probe and through a second light conductor to the radiation detector and the radiation evaluator, and an indicator for the indication of a measurement result determined by the radiation evaluator on the basis of the detected response radiation, wherein the first and second light conductors are coupled into the light fiber bundle to transmit the radiation from the first light conductor to the tooth tissue region and to receive the response radiation from the tooth tissue region to the second light conductor, wherein the excitation radiation generator and the radiation detector are integrated in a dental handpiece, wherein the radiation detector includes a photodiode for the detection of the response radiation, which photodiode is arranged in the handpiece at an end of the second light conductor for the transmission of the response radiation, and wherein the photodiode is arranged behind an opening into which the second light conductor opens out.

2. Dental device for the investigation of the optical properties of tooth tissue, comprising an excitation radiation generator, which radiation is to be directed onto a tooth tissue region to be investigated, a radiation detector and a radiation evaluator for the detection and evaluation of a response radiation arising from the irradiated tooth tissue region in response to the irradiation, wherein a light conductor transmits the response radiation from the tooth tissue region to be investigated to the radiation detector and the radiation evaluator, and the radiation detector is surrounded by a housing arranged within a dental handpiece, the housing having a cylindrical opening including a snap fastening in a forward end of the housing, the opening for receiving the light conductor and the snap fastening for holding the light conductor so that the response radiation is directed onto the radiation detector; and an indicator for indicating a measurement result determined by the radiation evaluator on the basis of the detected response radiation, wherein the excitation radiation generator and the radiation detector are integrated in the dental handpiece, at least the indicator is also arranged in or on the handpiece, the handpiece includes a removable sleeve which is made of sterilizable material, the removable sleeve surrounds at least a forward region of the handpiece, the radiation detector includes an elongate light wedge attached at the forward end of the handpiece, and the elongate light wedge is configured to direct the radiation onto the tooth tissue region laterally of a longitudinal axis of the light wedge.

3. Device according to claim 1, wherein the photodiode is surrounded by a housing arranged within the dental handpiece, the housing having an opening in a forward end of the housing, the opening for receiving the second light conductor.

* * * * *